United States Patent
Sato et al.

(10) Patent No.: US 9,146,314 B2
(45) Date of Patent: Sep. 29, 2015

(54) ULTRASONIC DIAGNOSTIC APPARATUS

(75) Inventors: Takeshi Sato, Nasushiobara (JP); Chihiro Shibata, Nasushiobara (JP)

(73) Assignees: KABUSHIKI KAISHA TOSHIBA, Tokyo (JP); Toshiba Medical Systems Corporation, Otawara-shi (JP)

( * ) Notice: Subject to any disclaimer, the term of this patent is extended or adjusted under 35 U.S.C. 154(b) by 296 days.

(21) Appl. No.: 13/152,920

(22) Filed: Jun. 3, 2011

(65) Prior Publication Data

US 2011/0301470 A1    Dec. 8, 2011

(30) Foreign Application Priority Data

Jun. 4, 2010 (JP) ................... 2010-129409

(51) Int. Cl.
*A61B 8/06* (2006.01)
*G01S 15/89* (2006.01)
*A61B 8/13* (2006.01)
*G01S 7/52* (2006.01)

(52) U.S. Cl.
CPC ............... *G01S 15/8981* (2013.01); *A61B 8/06* (2013.01); *A61B 8/13* (2013.01); *G01S 7/52085* (2013.01)

(58) Field of Classification Search
CPC ........ A61B 8/488; A61B 8/5207; A61B 8/06; A61B 8/13
USPC .......................................... 600/407, 437–472
See application file for complete search history.

(56) References Cited

U.S. PATENT DOCUMENTS

| | | | |
|---|---|---|---|
| 5,188,113 A | 2/1993 | Sato et al. | |
| 5,642,732 A * | 7/1997 | Wang | ............................ 600/453 |
| 6,508,766 B2 | 1/2003 | Sato et al. | |
| 6,558,325 B1 * | 5/2003 | Pang et al. | ..................... 600/443 |
| 2001/0025143 A1 | 9/2001 | Suzuki | |
| 2006/0020205 A1 | 1/2006 | Kamiyama | |
| 2007/0239015 A1 | 10/2007 | Sato | |
| 2008/0242982 A1 | 10/2008 | Tamura | |

(Continued)

FOREIGN PATENT DOCUMENTS

| EP | 1 136 841 A2 | 9/2001 |
|---|---|---|
| EP | 1 136 841 A3 | 9/2001 |

(Continued)

OTHER PUBLICATIONS

U.S. Appl. No. 13/688,556, filed Nov. 29, 2012, Sato.

(Continued)

*Primary Examiner* — Mark Remaly
(74) *Attorney, Agent, or Firm* — Oblon, McClelland, Maier & Neustadt, L.L.P.

(57) ABSTRACT

In one embodiment, a scanning unit repeatedly scans an internal region of an object with an ultrasonic wave at a predetermined frame rate via an ultrasonic probe. An image generation unit extracts a blood flow signal based on a Doppler effect from a reflection signal and repeatedly generates a blood flow image representing a spatial distribution associated with power of the blood flow signal at the frame rate. A power average value associated with a frame or local region is calculated for the blood flow image. The blood flow image is corrected. In the correcting, a gain on the power values in the frame or local region in which the power average value exceeds the threshold are substantially reduced, and power values in the frame or local region in which the power average value is not more than the threshold are maintained.

16 Claims, 6 Drawing Sheets

(56) References Cited

U.S. PATENT DOCUMENTS

2009/0112096 A1    4/2009   Tamura
2009/0251570 A1*   10/2009   Shi ............................ 348/241

FOREIGN PATENT DOCUMENTS

| | | |
|---|---|---|
| EP | 1 614 387 A1 | 1/2006 |
| JP | 7-79976 | 3/1995 |
| JP | 8-336534 | 12/1996 |
| JP | 10-99333 | 4/1998 |
| JP | 11-267125 | 10/1999 |
| JP | 11-318902 | 11/1999 |
| JP | 2001-149370 | 6/2001 |
| JP | 2001-269344 | 10/2001 |
| JP | 3724846 | 9/2005 |

OTHER PUBLICATIONS

Extended European Search Report issued Sep. 23, 2011, in European Patent Application No. 11250577.1.

Office Action mailed Jan. 7, 2014, in Japanese Patent Application No. 2010-129409 (with English-language Translation).

* cited by examiner

Without motion artifact and power correction | Without motion artifact and with power correction

FIG. 7

With motion artifact and without power correction | With motion artifact and with power correction

FIG. 8

ULTRASONIC DIAGNOSTIC APPARATUS

CROSS-REFERENCE TO RELATED APPLICATIONS

This application is based upon and claims the benefit of priority from Japanese Patent Application No. 2010-129409, filed Jun. 4, 2010; the entire contents of which are incorporated herein by reference.

FIELD

Embodiments described herein relate generally to an ultrasonic diagnostic apparatus.

BACKGROUND

A color Doppler method in ultrasonic diagnosis is configured to transmit an ultrasonic wave to a living body in the same direction a plurality of number of times. This method extracts blood flow information such as the velocities, variances, and powers of blood flows from a plurality of echoes using the Doppler effect. Echo data strings, of the data obtained by plural emissions of ultrasonic waves in the same direction, which are associated with the same point (the same depth point on the same ultrasonic raster) are called packets. The packet size is set to about 5 to 16, that is, packets are made uniform by emitting ultrasonic waves 5 to 16 times in the same direction. A blood flow signal is extracted from a packet by applying to it a wall filter for suppressing signals from the tissue, i.e., clutter signals, thereby displaying blood flow information such as a velocity, variance, and power. For this reason, the following problem arises.

A packet is closed within an ultrasonic scan frame. Therefore, as the packet size increases, the framer rate decreases. An IIR filter is often used as a wall filter. With a small packet size, however, a transient response occurs in the IIR filter, resulting in a deterioration in the characteristics of the IIR filter.

Studies have therefore been made on a method of handling signals at the same position between frames as a packet instead of handling a packet as a closed packed in a frame. In this method, since a pulse repetition frequency (PRF) is equal to a frame rate, the aliasing velocity becomes low to allow even low flow rate observation. However, the method makes it easy for clutter signals from the tissue to pass through a wall filter, and hence motion artifacts tend to occur. When, in particular, the operator moves the probe gripped by his/her hand, an entire window is displayed with clutter noise. This problem arises not only in the above scanning method but also in general color Doppler scanning operation when the aliasing velocity is low.

DETAILED DESCRIPTION

In general, according to one embodiment, an ultrasonic diagnostic apparatus comprises an ultrasonic probe, a scanning unit configured to repeatedly scan an internal region of an object with an ultrasonic wave at a predetermined frame rate via the probe, and an image generation unit configured to extract a blood flow signal based on a Doppler effect from a reflection signal obtained by the scan and repeatedly generate a blood flow image representing a spatial distribution associated with power of the blood flow signal at the frame rate. In this embodiment, a power average value associated with a frame or local region is calculated for the blood flow image. The blood flow image is corrected by processing of substantially reducing a gain on the power values in the frame or local region in which the power average value exceeds the threshold, and maintaining power values in the frame or local region in which the power average value is not more than the threshold. With this correction, when there is no motion artifact, the power of a blood flow is displayed. When motion artifacts occur, the gain reduction processing functions to allow observation of a tissue structure.

More specifically, this embodiment logarithmically compresses the power of a Doppler signal (blood flow signal) after passing through a wall filter, and calculates a power average value for an entire frame or each local area of the obtained blood flow image. If this power average value exceeds a given threshold, a value corresponding to the difference between the power average value and the threshold is subtracted from the power value of each pixel. If the power average value is equal to or less than the threshold, the power value of each pixel after logarithmic compression is maintained without the execution of the above subtraction for the power value of each pixel after the logarithmic compression. This processing is called power correction.

Figure 7:
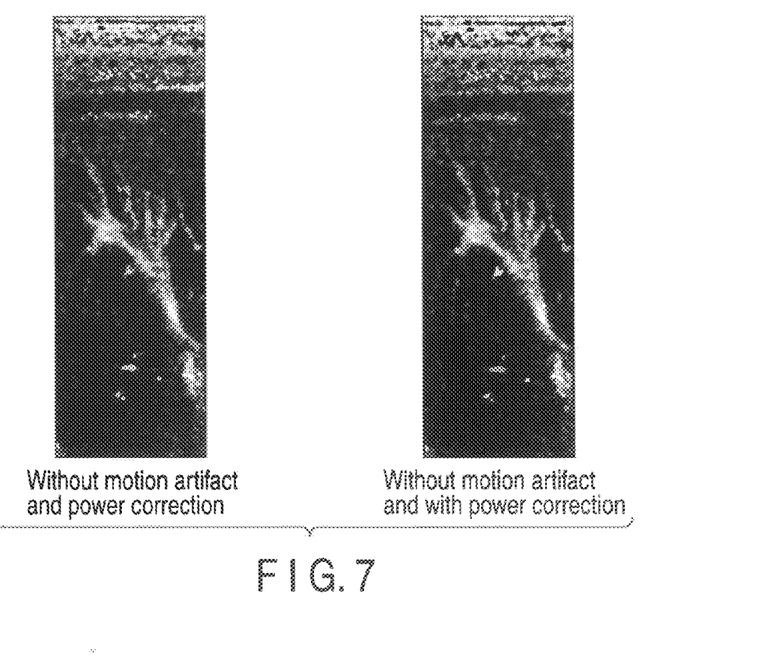
FIG. 7 is a view showing the effect of power correction in this embodiment without any motion artifacts.
Figure 8:
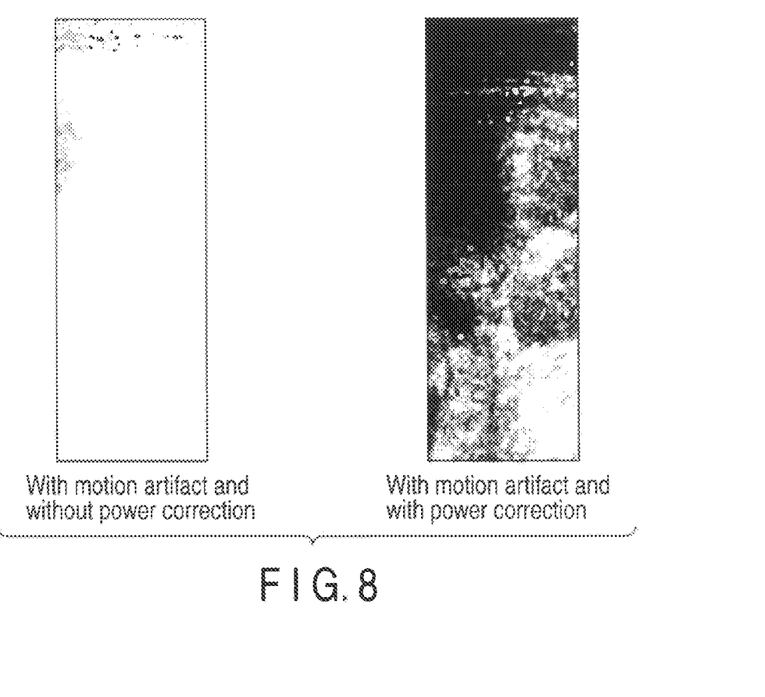
FIG. 8 is a view showing the effect of power correction in this embodiment with motion artifacts.

If many low-frequency components (mainly clutter components) other than blood flow components remain in a Doppler signal (blood flow signal) after passing through the wall filter, the remaining components fill an image display window with white, which corresponds the maximum display gray level in grayscale display of powers (the left image in FIG. 8). With the above processing in this embodiment, that is, the subtraction processing after logarithmic compression, which is equivalent to the processing of reducing the gain on a linear axis, the remaining components are shaded and can be visually recognized as a tissue image (the right image in FIG. 8). That is, as shown in FIG. 7, the power of a blood flow is displayed without any motion artifacts regardless of whether power correction is executed, whereas when motion artifacts occur, a tissue image can be seen.

As described above, in this embodiment, the power of a blood flow is displayed without any motion artifacts, but a tissue image is seen when motion artifacts occur. This makes it possible to continue scanning, even when the operator moves the probe, while visually checking a tissue image, unlike the prior art in which when the operator moves the probe, he/she cannot continue scanning because a window becomes totally white due to motion artifacts.

Figure 1:
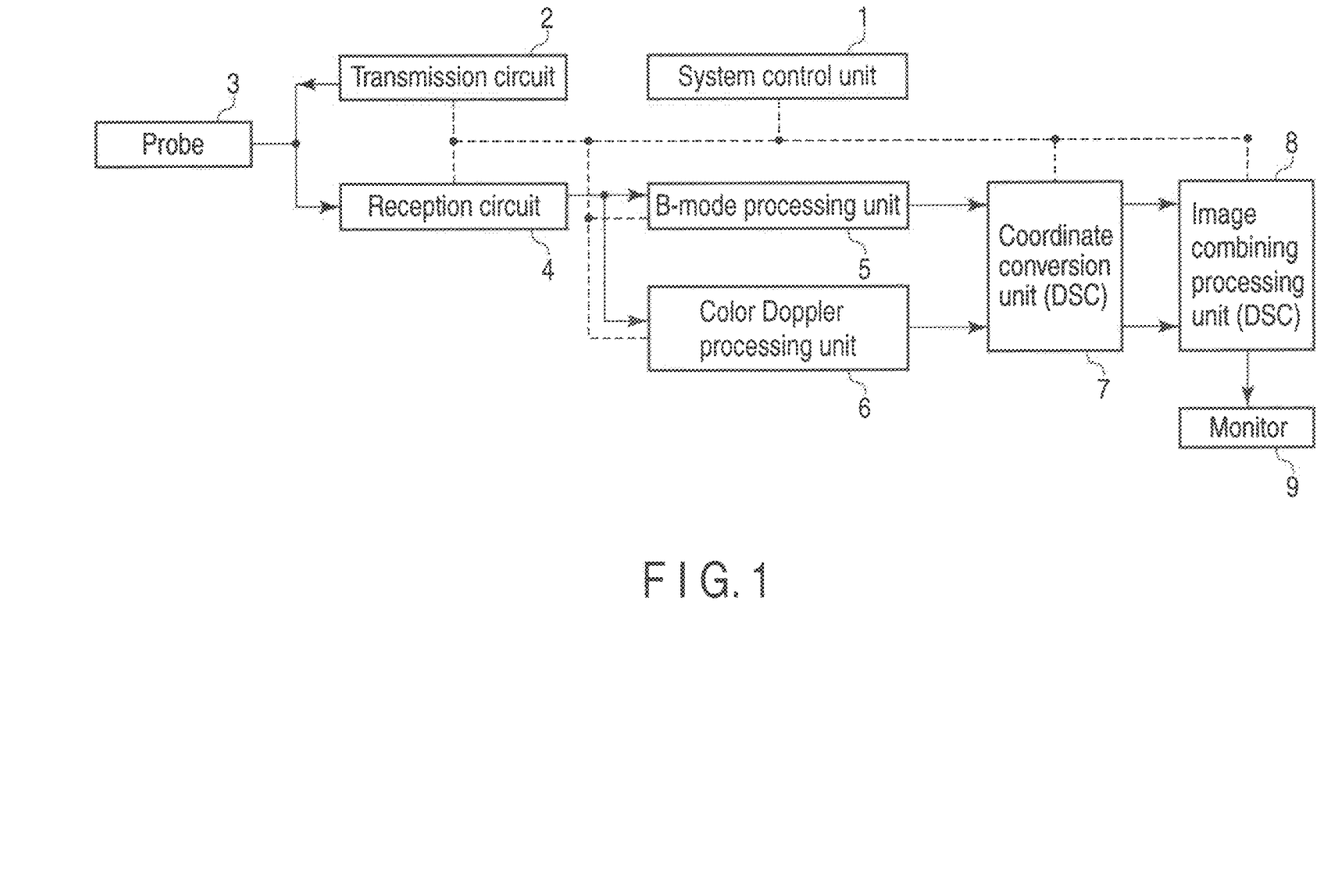
FIG. 1 is a block diagram showing the arrangement of an ultrasonic diagnostic apparatus according to an embodiment.

FIG. 1 shows the arrangement of an ultrasonic diagnostic apparatus according to this embodiment. A control unit 1 serves as the main control unit of the overall apparatus and is in charge of scanning control, in particular. An ultrasonic probe 3 includes a plurality of piezoelectric elements as electromechanical transducers. In order to electronically perform three-dimensional scanning, for example, the plurality piezoelectric elements are arranged two-dimensionally. Electronic three-dimensional scanning is a scheme in which the directivity of an ultrasonic beam is changed by changing delay control in a planar direction almost perpendicular to a scan surface as well as in an azimuth direction, thereby scanning a three-dimensional region in an object thoroughly with ultrasonic waves. Note that in this case, the operation of scanning an internal region of an object thoroughly is defined as a unit of scanning. A scan to be performed is not limited to a sequential scan to sequentially move ultrasonic scanning lines in accordance with the array of ultrasonic scanning lines, and may be a discrete scan to discretely move ultrasonic scanning lines irrelevantly to the array of ultrasonic scanning lines.

A transmission circuit 2 and a reception circuit 4 are connected to the probe 3. The transmission circuit 2 includes a pulse generator, a transmission delay circuit, and a pulser. The pulse generator generates rate pulses at a rate frequency of, for example, 6 kHz. These rate pulses are distributed according to the number of channels and sent to the transmission delay circuit. The transmission delay circuit gives each rate pulse a delay time necessary to focus an ultrasonic wave into a beam and determine transmission directivity. The pulser applies a voltage pulse to the probe 3 at the timing when a rate pulse is received from the transmission delay circuit. This causes the probe 3 to transmit an ultrasonic pulse into the object. The probe 3 receives the waves reflected by a discontinuity surface of acoustic impedance in the object. A reception signal from the probe 3 is input to the reception circuit 4. The reception circuit 4 includes a preamplifier, a reception delay circuit, an adder, a quadrature detection circuit, and a low-pass filter. The preamplifier amplifies a reception signal for each channel. The reception delay circuit gives the amplified signals delay times necessary to determine reception directivities. The adder then adds them to obtain a reflection signal with a reflection component from a direction corresponding to reception directivity being enhanced.

In the B mode, the reflection signal is sent to a B-mode processing unit 5 without being changed. The B-mode processing unit 5 logarithmically amplifies the reflection signal and detects it to generate a tissue image (B-mode image) representing a tissue morphology. A coordinate conversion unit 7, which is also called a digital scan converter (DSC), rearranges the B-mode image according to the scanning system of a monitor 9. The monitor 9 then displays the image.

In the Doppler mode, a reflection signal is sent as a complex signal (IQ signal) constituted by a real part and imaginary part associated with a Doppler shift component to the color Doppler processing unit 6 via the quadrature detection circuit and the low-pass filter. The color Doppler processing unit 6 extracts a high-frequency blood flow signal by removing low-frequency clutter components from the IQ signal associated with the Doppler shift via a high-pass wall filter, and calculates the average velocity, variance, and power of the signal. The average velocity, variance, and power are displayed individually or in arbitrary combination with each other on the monitor 9 via the coordinate conversion unit 7. An image combining processing unit 8 can arbitrarily combine the blood flow image with a B-mode image.

Figure 2:
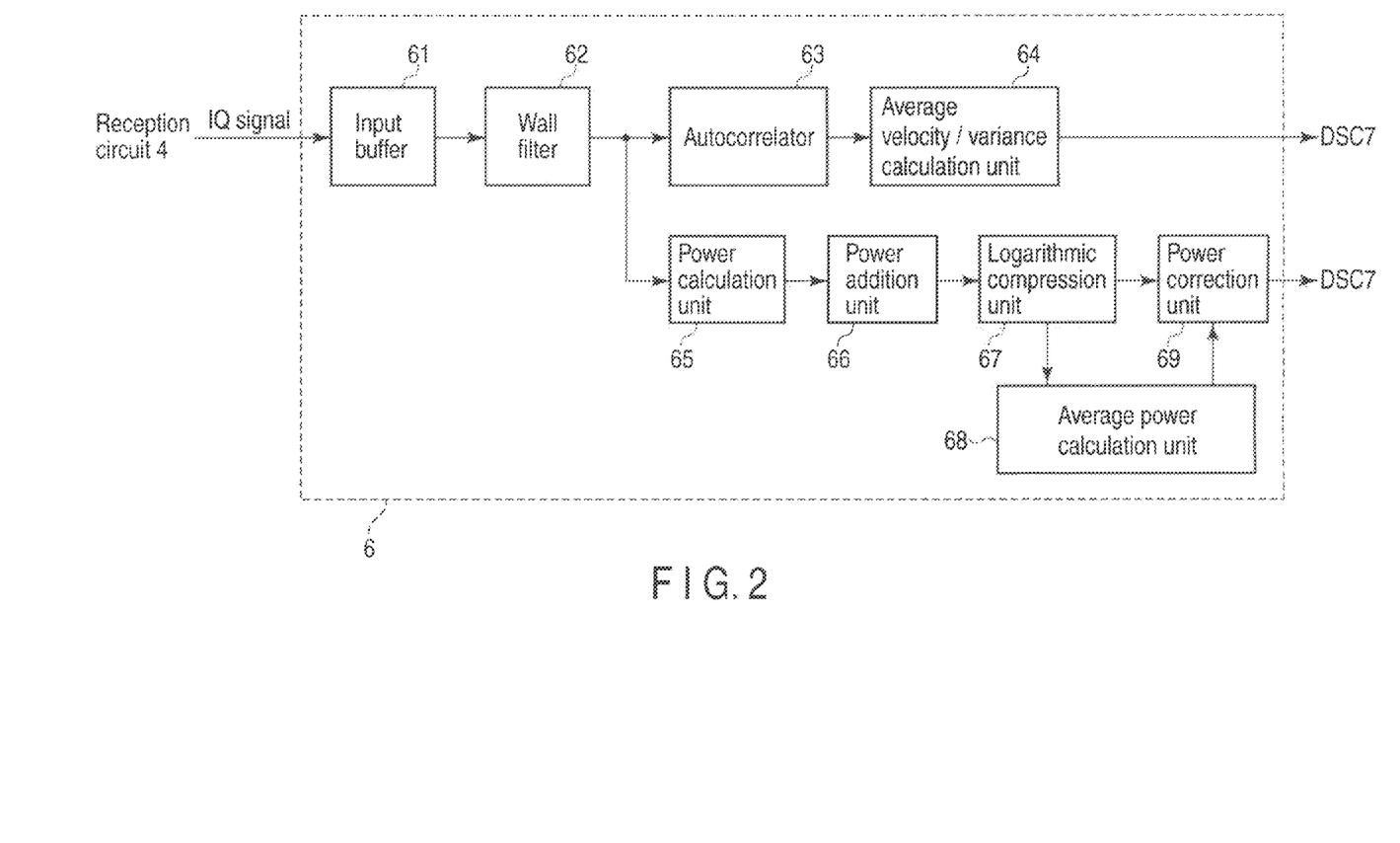
FIG. 2 is a block diagram showing the arrangement of a color Doppler processing unit in FIG. 1.

FIG. 2 shows the arrangement of the color Doppler processing unit 6 in FIG. 1. An input buffer 61 holds IQ signals, rearranges the signals into data strings for the respective ultrasonic scanning lines and depths, and outputs the data strings for each data unit called a packet having a predetermined length. In the Doppler mode according to this embodiment, a unit scan is repeated as in the B-mode scanning mode. A unit scan is the operation of scanning an internal region thoroughly while changing an ultrasonic scanning line (azimuth) for each ultrasonic transmission/reception. The time required to scan an internal region thoroughly is called a scan period, and the reciprocal of the period is called a frame rate. That is, a frame rate is the number of times of scanning the internal region per sec. In the Doppler mode, blood flow information is calculated based on an echo data string (packet data) associated with the same point (a point at the same depth in the same azimuth) of data obtained by plural emissions of ultrasonic waves in the same direction. The pulse repetition frequency (PRF) associated with this packet data is equivalent to a frame rate. This scanning method can theoretically obtain packet data up to infinite length. In practice, however, an arbitrary packet size is selected from the range of 5 to 16. It is possible to sequentially generate packet data in a scan cycle by repeating the processing of adding new echo data and removing old echo data.

A wall filter 62 has a high-pass characteristic for removing, from packet data, low-frequency clutter components originating from a reflector whose motion velocity is low such as the cardiac muscle and extracting blood flow components with relatively high frequencies. The IQ data associated with a blood flow and output from the wall filter 62 is sent to an autocorrelator 63 and a power calculation unit 65. The autocorrelator 63 obtains an autocorrelation value by taking the complex conjugate between the IQ data of the blood flow in the current frame and the IQ data of the blood flow in a frame immediately preceding the current frame. An average velocity is obtained by calculating the angle defined by a real part and an imaginary part from this correlation data.

The power calculation unit 65 calculates powers representing the intensities of scattering by a reflector (blood cells) having a lower frequency than ultrasonic waves at multiple points by adding the squares of the absolute values of the real and imaginary parts of the IQ data associated with the blood flow and output from the wall filter 62. A power addition unit 66 adds the powers at the respective points within a packet. A logarithmic compression unit 67 logarithmically compresses the power addition value. An average power calculation unit 68 calculates an average power value in one frame or local region from the compressed power addition value. For a pixel whose average power value exceeds a threshold, a power correction unit 69 subtracts the value obtained by multiplying the difference between the average power value and the threshold by a coefficient from the power value of the pixel. When low-frequency components, mainly clutter components, other than blood flow components remain in a Doppler signal (blood flow signal) after passing through the wall filter, the clutter components exhibit higher power than the blood flow components. Therefore, the average power value is higher than the threshold. By subtracting the value obtained by multiplying the difference between the average power value and the threshold by the coefficient from the power value of each pixel from which the average power value is calculated, it is possible to avoid a situation in which remaining components mainly including clutter components fill, as motion artifacts, an image display window with white, which corresponds the maximum display gray level in grayscale display of powers, thereby suppressing changes within a display grayscale range. This makes it possible to display, as intensity changes, a tissue morphology which remaining components generated in large quantities upon movement of the probe essentially have.

This power correction will be described in detail below. As described above, blood flow powers are displayed in gray-scale. It is preferable to transmit and receive ultrasonic waves under conditions similar to those in the B mode instead of those in the color Doppler mode. The IQ signal held in the input buffer 61 is rearranged into a string of signals from the same position. The signal string is output to the wall filter 62. The wall filter 62 removes fixed signals and signals representing slow movement, mainly clutter signals, by using its high-pass characteristics. The power calculation unit 65 calculates the square of the absolute value of an output signal from the wall filter 62. The power calculation unit 65 then adds the data in the packet to the signal. The logarithmic compression unit 67 logarithmically compresses the resultant signal. The average power calculation unit 68 calculates the average power of the compressed power signal in the frame or local region. The power correction unit 69 performs the following correction processing:

If
power value of given pixel (position): Pin
average power value: Pm
threshold: Pth
gain correction coefficient: a
power value after correction: Pout
then, $$Pout=Pin(\text{if } Pm \leq Pth)$$

$$Pout=Pin-a \times (Pm-Pth)(\text{if } Pm > Pth)$$

In this case, if a power value corresponding to the maximum display gray level is Dmax,
then, values similar to the following values are preferable:

$$Pth=Dmax/2$$

$$a=0.75 \text{ to } 1.0$$

That is, the gain of the power value of a pixel in a frame or local region in which the average power exceeds the threshold is substantially reduced in accordance with the power average value and the threshold. The power value of a pixel in a frame or local region in which the average power is equal to or less than the threshold is maintained.

The coordinate conversion unit 7 performs coordinate conversion of this power value. The monitor 9 then displays the resultant data. This data is suitably displayed in grayscale.

Such power correction processing has the following effects.

Figure 3:
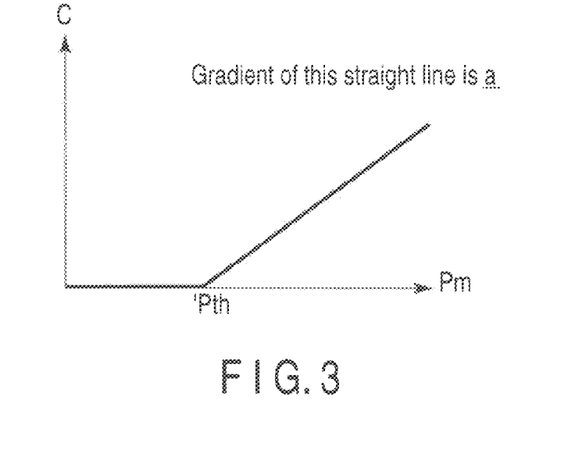
FIG. 3 is a graph for explaining correction coefficients used by a power correction unit in FIG. 2.

For the sake of convenience, if a correction formula is expressed in the form of Pout=Pin−C where C is a gain correction value. The value of C can be expressed by the graph shown in FIG. 3. If there is no motion artifact, since the wall filter 62 sufficiently suppresses clutter signals from the tissue, the average power becomes a value much smaller than the maximum value in display. For this reason, Pm≤Pth, and an output value from the power correction unit 69 is equal to the input value, as described above. If, for example, motion artifacts occur due to the movement of the probe 3, clutter signals from the tissue pass through the wall filter 62 without being sufficiently suppressed. In this case, the range of the clutter signals spreads on the entire window. For this reason, average power value Pm>Pth, and is corrected into Pout=Pin−a×(Pm−Pth). This output is the value obtained by subtraction from the logarithmically compressed signal. This processing is therefore essentially equivalent to the processing of reducing the gain relative to the original power signal on the linear axis. The motion artifacts passing through the wall filter 62 are clutter signals from the tissue, and hence are essentially equivalent to a B-mode signal. The gain is high under the conditions for the display of a blood flow, and hence the motion artifacts are displayed in totally white which almost corresponds the maximum display gray level. However, since the gain is substantially reduced by the correction processing in this embodiment, if motion artifacts occur, they are displayed as a tissue morphology image similar to that in the B mode. With this operation, when the probe 3 is at rest, the power of a blood flow is displayed, whereas when the probe 3 is moved, a tissue morphology image is displayed.

According to the above description, the average power value of an overall frame is obtained. However, it is possible to obtain the average power of each block upon dividing a frame into a plurality of local regions (blocks) and perform the above correction processing for each block. It is possible to reduce the discontinuity between the blocks by making the blocks overlap each other and continuously changing weights for the two blocks in each portion where they overlap each other.

Figure 4:
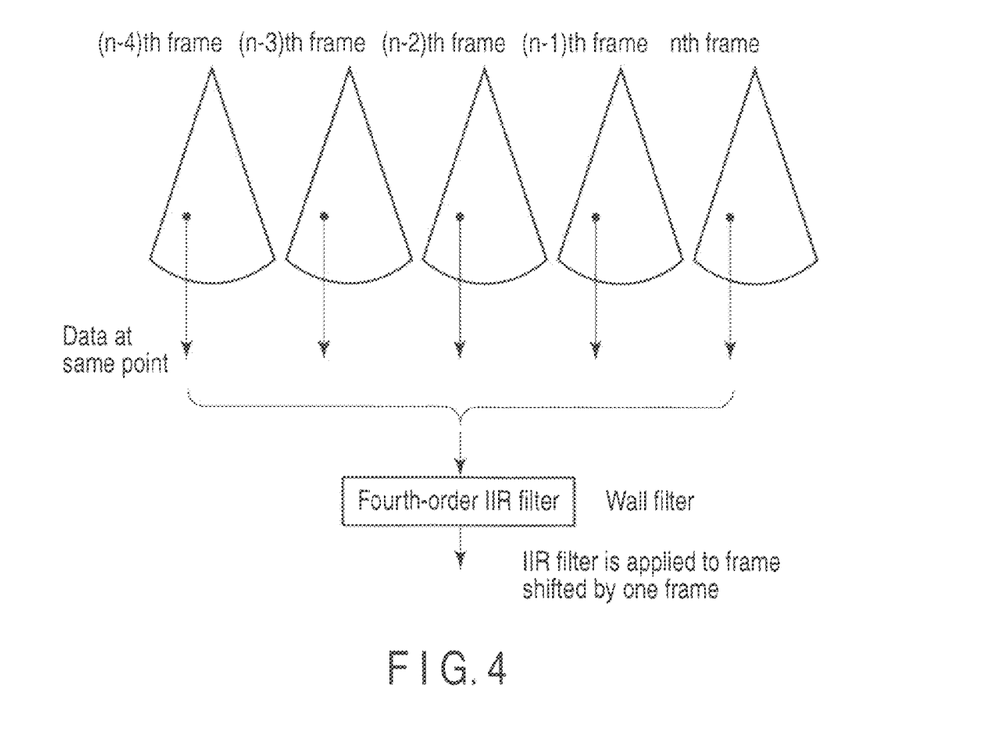
FIG. 4 is a view for explaining the processing performed by a wall filter in FIG. 2.

The Doppler mode generally repeats ultrasonic transmission/reception for each ultrasonic scanning line a predetermined number of times, i.e., 5 to 16 times, in a predetermined cycle (1/PRF) and sequentially moving an ultrasonic scanning line. In a scanning procedure in this embodiment shown in FIG. 4, an ultrasonic scanning line is sequentially moved while an ultrasonic wave is transmitted/received once for each of a plurality of ultrasonic scanning lines constituting an internal region (frame) of an object as a scan target. A unit scan, i.e., scanning a frame thoroughly, is continuously repeated. This scanning procedure is the same as that for a B-mode scan. Data strings from the same position between frames are used as packets. In this scanning procedure, an ultrasonic wave is repeatedly and intermittently transmitted and received to and from each ultrasonic scanning line in a predetermined scan cycle. As the wall filter 62, a fourth-order IIR filter can be used. The input buffer 61 stores data ranging from at least six frames preceding the current frame to the current frame. The IIR filter represented by the following equation is applied to signals from the same positions.

$$y(n) = b0*x(n) + b1*x(n-1) + b2*x(n-2) + b3*x(n-3) + b4*x(n-4) + a1*y(n-1) + a2*y(n-2) + a3*y(n-3) + a4*y(n-4)$$

where x(n) is an IQ signal of the current frame, x(n−1) is an IQ signal of a frame immediately preceding the current frame, y(n) is an output from the wall filter 62, and y(n−1) is a wall filter output corresponding to a frame immediately preceding the current frame. According to the general operation procedure described above, since the packet length is limited to 5 to 16, which is the number of times of repetition of transmission/reception, a transient response occurs when an IIR filter is used. For this reason, the first two to four data cannot be used. In contrast to this, in this scanning procedure, since data of infinite length are continuously input, no transient response problem occurs. It is also possible to increase the order of the IIR filter. This improves the performance of the wall filter 62 as compared with the prior art.

The power calculation unit 65 then calculates powers. The power addition unit 66 calculates a moving average between an arbitrary number of consecutive frames. One of the advantages of this scanning procedure is that it is possible to arbitrarily set the number of times of power addition. The subsequent processing is the same as that described above.

In this scanning procedure, the pulse repetition frequency (PRF) is equal to the frame rate and can be suppressed considerably low as compared with the above general scanning procedure in which ultrasonic transmission/reception is repeated for each ultrasonic scanning line. This allows observation of even blood flows of low flow rates. On the other hand, motion artifacts tend to occur due to the movement of the tissue. If the motion artifacts are displayed without any change, since the power values are large, the window is displayed totally white. In this scanning procedure, when motion artifacts occur, since the average power Pm becomes larger than Pth, only a value dependent on the average power value Pm is subtracted from the original power value. Since this subtraction is performed after logarithmic compression, the subtraction on the linear axis is essentially equivalent to division processing. This obtains the effect of automatically reducing the gain. Since a motion artifact is an echo signal from the tissue, the image whose gain is reduced is an image equivalent to an image of the tissue, i.e., a B-mode image. This makes it possible to continue scanning without any sense of discomfort.

It is also possible to use the following Doppler scanning together with B-mode scanning. In the above two types of scanning procedures, Doppler scanning is independently performed based on the assumption that only the power of a blood flow is displayed. According to the scanning procedure shown in FIG. 5, a unit scan is repeated under transmission/reception conditions for the Doppler mode of scanning an internal region thoroughly while changing an ultrasonic scanning line every time an ultrasonic wave is transmitted/received once. In the process of repeating this unit scan, the transmission/reception conditions for the Doppler mode are switched to the transmission/reception conditions for the B mode once per a predetermined number of scans, once per five scans in the case shown in FIG. 5, to insert one or two unit scans under the transmission/reception conditions for the B mode. The transmission/reception conditions for the B mode include a lower central transmission frequency, a larger number of ultrasonic scanning lines, a larger view angle, and a larger depth of field than the transmission/reception conditions for the Doppler mode.

This scanning procedure allows to display a general B-mode image concurrently with the display of the power of a blood flow. The following are two different concrete methods.

In the first method, B-mode image processing and blood flow power display processing share the same reflection signal. Images may be superimposed/displayed or separately displayed in two different windows. This method repeats a unit scan under the fixed transmission/reception conditions for the Doppler mode without switching the transmission/reception conditions for the Doppler to those for the B mode, and hence has disadvantages in terms of the S/N ratio of a B-mode image, view angle, and depth of field.

Figure 5:
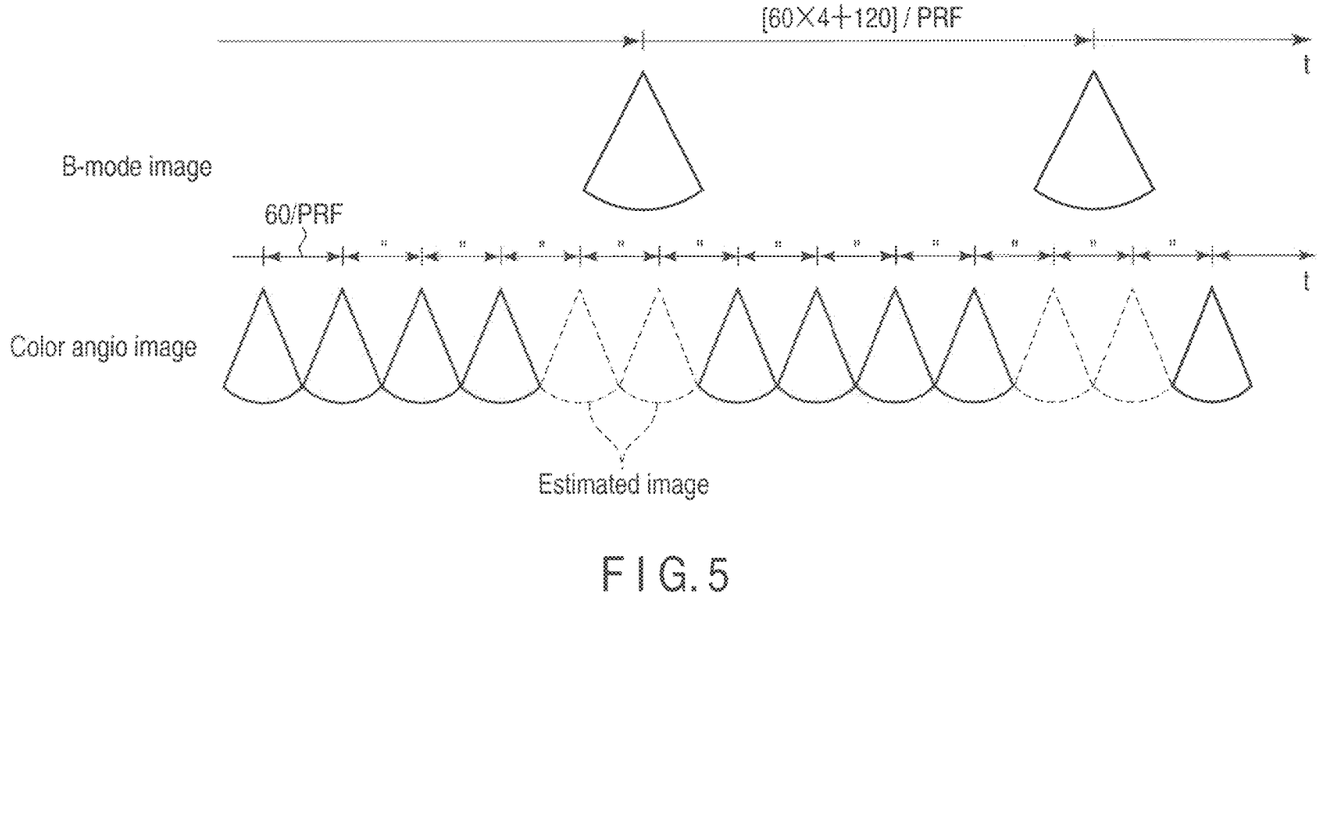
FIG. 5 is a view showing another scanning procedure executed by a transmission circuit and reception circuit in FIG. 1.
Figure 6:
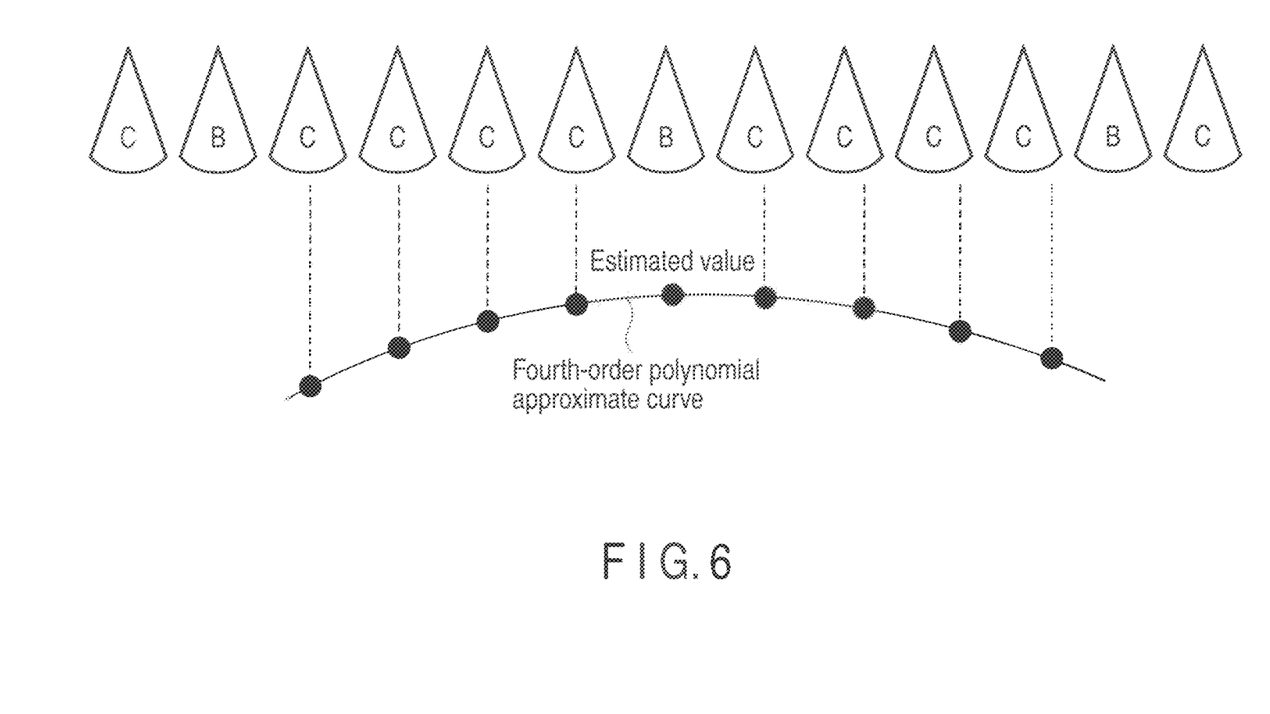
FIG. 6 is a view showing interpolation processing for a blood flow image by an average power calculation unit in FIG. 1.

The second method performs transmission/reception under different transmission/reception conditions instead of using the same reflection signal for a B-mode image and a blood flow image, and uses signals optimized for the respective images. As shown in FIG. 5, according to this scanning procedure, a B-mode scan is performed under the transmission/reception conditions for the B mode once per five unit scans in the Doppler mode. Although data for a blood flow in this B-mode scan period is lost, the blood flow data in the period is estimated and interpolated from blood flow data acquired by Doppler scans adjacent through the B-mode scan period, as shown in FIG. 6. As an estimation method, the least squares method is used. Polynomial approximation (e.g., fourth-order approximation) is performed from four data on each of the two sides, i.e., a total of eight data, and the least squares method is then used to estimate a coefficient to estimate central data. Filling the lost data by estimation in this manner allows to handle the resultant data as continuous data. Note that to use this method, the scan time taken for a frame for the B mode needs to be equal to or an integer multiple of the scan time taken for a frame for a blood flow.

Note that if the scan time in the B mode is not an integer multiple of that for a blood flow, an IIR wall filter which allows the effective use of data of infinite length with a simple arrangement cannot be used, but a wall filter using the least squares method can be used.

In this manner, a signal for the B mode and a signal for a blood flow are separately obtained, and the resultant images are displayed in two windows or superimposed/displayed in the same manner as that in the first method.

According to the above description, grayscale display is suitable as a display scheme to be used. However, it is possible to perform color display by using both information output from the power correction unit 69 and information output from an average velocity/variance calculation unit 64. For example, displaying a positive velocity, negative velocity, and power value by using a red hue, blue hue, and brightness, respectively, allows to display the information of a blood flow direction in color and observe the moving state of blood cells as luminance changes. In addition, using a white hue in accordance with the amount of power correction performed will display a tissue component having undergone power correction in grayscale and display a blood flow component not having undergone power correction in a red or blue hue. It is also possible to perform color display by using a two-dimensional or three-dimensional color map exhibiting continuous changes in accordance with power values and velocity values and/or variance values.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnostic apparatus, comprising:
   an ultrasonic probe;
   a scanning circuit that includes a transmission circuit and a reception circuit and is configured to perform a scan of an internal region of an object with an ultrasonic wave at a predetermined frame rate via the ultrasonic probe;
   a processor configured to
      extract a Doppler signal based on a Doppler effect from a reflection signal obtained by the scan and generate a Doppler signal image representing a spatial distribution associated with power of the Doppler signal;
      calculate a power average value in a frame of the Doppler signal image;
      compare the calculated power average value to a threshold; and
      perform processing of reducing power values of pixels in the frame of the Doppler signal image in which the power average value exceeds the threshold, to generate a corrected Doppler signal image.

2. The apparatus of claim 1, further comprising a display configured to display the Doppler signal image in colors corresponding to at least one of a power value of the corrected Doppler signal image, a difference between the power average value and the threshold, a fluid rate corresponding to the Doppler signal, and a variance of the fluid corresponding to the Doppler signal.

3. The apparatus of claim 1, wherein the scanning circuit repeats the scan to scan the internal region thoroughly while changing an ultrasonic scanning line every time the ultrasonic wave is transmitted and received once.

4. The apparatus of claim 1, wherein the scanning circuit repeats a unit scan to scan the internal region thoroughly while changing an ultrasonic scanning line every time the ultrasonic wave is transmitted and received, and switches a transmission or reception condition for a Doppler mode to a transmission or reception condition for a B mode at a frequency of once per a predetermined number of times of execution of the unit scan during repetition of the unit scan.

5. The apparatus of claim 4, wherein the processor is further configured to estimate, by a least squares method, and interpolate a Doppler signal image that was lost due to switching to the transmission or reception condition for the B mode from a Doppler signal image acquired under the transmission or reception condition for the Doppler mode.

6. The apparatus of claim 1, wherein the scanning circuit scans the internal region according to a three-dimensional scanning procedure.

7. An ultrasonic diagnostic apparatus, comprising:
an ultrasonic probe;
a scanning circuit that includes a transmission circuit and a reception circuit and is configured to perform a scan of an internal region of an object with an ultrasonic wave at a predetermined frame rate via the ultrasonic probe;
a processor configured to
extract a Doppler signal from a reflection signal obtained by the scan based on a Doppler effect and generate a Doppler signal image representing a spatial distribution associated with power of the Doppler signal;
logarithmically compress a power value of each pixel of the Doppler signal image to generate a compressed Doppler signal image;
calculate a power average value associated with a frame for the compressed Doppler signal image;
compare the calculated power average value to a threshold; and
perform processing of reducing power values of pixels in the frame of the Doppler signal image in which the power average value exceeds the threshold to generate a corrected Doppler signal image.

8. The apparatus of claim 7, further comprising a display configured to display the Doppler signal image in colors corresponding to at least one of a power value of the corrected Doppler signal image, a difference between the power average value and the threshold, a fluid rate corresponding to the Doppler signal, and a variance of the fluid corresponding to the Doppler signal.

9. The apparatus of claim 7, wherein the scanning circuit repeats the scan to scan the internal region thoroughly while changing an ultrasonic scanning line every time the ultrasonic wave is transmitted/received once.

10. The apparatus of claim 7, wherein the scanning circuit repeats a unit scan to scan the internal region thoroughly while changing an ultrasonic scanning line every time the ultrasonic wave is transmitted and received, and switches a transmission or reception condition for a Doppler mode to a transmission or reception condition for a B mode at a frequency of once per a predetermined number of times of execution of the unit scan during repetition of the unit scan.

11. The apparatus of claim 10, wherein the processor is further configured to estimate, by a least squares method, and interpolate a Doppler signal image that was lost due to switching to the transmission or reception condition for the B mode from a Doppler signal image acquired under the transmission or reception condition for the Doppler mode.

12. The apparatus of claim 7, wherein the scanning circuit scans the internal region according to a three-dimensional scanning procedure.

13. An ultrasonic diagnostic apparatus, comprising:
an ultrasonic probe;
a scanning circuit that includes a transmission circuit and a reception circuit and is configured to perform a scan of an internal region of an object with an ultrasonic wave via the ultrasonic probe; and
a processor configured to generate an image using a reflection signal obtained by the scan,
wherein the scanning circuit repeats a unit scan to scan the internal region thoroughly while changing an ultrasonic scanning line every time the ultrasonic wave is transmitted and received, and switches a transmission or reception condition for a Doppler mode to a transmission or reception condition for a B mode at a frequency of once per a predetermined number of times of execution of the unit scan during repetition of the unit scan.

14. The apparatus of claim 13, wherein the processor is further configured to estimate, by a least squares method, and interpolate a Doppler signal image that was lost due to switching to the transmission or reception condition for the B mode from a Doppler signal image acquired under the transmission or reception condition for the Doppler mode.

15. The ultrasonic diagnostic apparatus of claim 1, wherein the processor is further configured to maintain power values for those pixels in the frame in which the power average value is not more than the threshold.

16. The ultrasonic diagnostic apparatus of claim 1, wherein the processor is further configured to reduce power values of the pixels in the frame by an amount proportional to a difference between the power average value and the threshold, when the power average value exceeds the threshold.

* * * * *